United States Patent
Davis

(10) Patent No.: US 10,561,665 B2
(45) Date of Patent: Feb. 18, 2020

(54) TREATMENT OF AUTISM

(71) Applicant: SYNAPTEC DEVELOPMENT LLC, Palm Beach Gardens, FL (US)

(72) Inventor: Bonnie M. Davis, Palm Beach Gardens, FL (US)

(73) Assignee: Synaptec Development LLC, Palm Beach Gardens, FL (US)

( * ) Notice: Subject to any disclaimer, the term of this patent is extended or adjusted under 35 U.S.C. 154(b) by 0 days.

(21) Appl. No.: 15/129,068

(22) PCT Filed: Mar. 24, 2015

(86) PCT No.: PCT/US2015/022220
§ 371 (c)(1),
(2) Date: Sep. 26, 2016

(87) PCT Pub. No.: WO2015/148487
PCT Pub. Date: Oct. 1, 2015

(65) Prior Publication Data
US 2017/0173038 A1    Jun. 22, 2017

Related U.S. Application Data

(60) Provisional application No. 61/969,896, filed on Mar. 25, 2014.

(51) Int. Cl.
*A61K 31/55* (2006.01)
*C07D 491/06* (2006.01)

(52) U.S. Cl.
CPC ............ *A61K 31/55* (2013.01); *C07D 491/06* (2013.01)

(58) Field of Classification Search
CPC ..................................................... A61K 31/55
USPC ......................................................... 514/215
See application file for complete search history.

(56) References Cited

U.S. PATENT DOCUMENTS 8,155,701 B2    4/2012  Balachandran et al.
2009/0253654 A1*  10/2009  Maelicke ............. C07D 307/91
                                                  514/81
2012/0009278 A1    1/2012  Perry

FOREIGN PATENT DOCUMENTS

WO    2006020852 A2    2/2006
WO    2010132423 A1    11/2010
WO    2011011766 A1    1/2011

OTHER PUBLICATIONS

McElhanon, Barbara O., et al. Gastrointestinal Symptoms in Autism Spectrum Disorder: A Meta-analysis. Pediatrics, May 2014, vol. 133, Issue 5.

(Continued)

*Primary Examiner* — Taofiq A Solola
(74) *Attorney, Agent, or Firm* — Ladas & Parry LLP

(57) ABSTRACT

Autistic Spectrum Disorders (ASD) are a group of developmental disorders including autistic disorder, Asperger disorder and pervasive developmental disorder not otherwise specified which may be treated by use of a galanthamine analog wherein the hydroxy group of galantamine is replaced by a carbamate, carbonate or ester group and the methoxy group may be replaced by another alkoxy group of from two to six carbon atoms, a hydroxy group, hydrogen, an alkanoyloxy group or 2 to 10 carbon atoms, a benzoyloxy or substituted benzoyloxy group, a carbonate group of 1 to 10 carbon atoms or a carbamate group such as a mono alkyl or dialkyl or an aryl carbamate wherein the alkyl groups or aryl groups contain from 1 to 10 carbons; and the N-methyl group may be replaced by hydrogen, alkyl of 1 to 10 carbon atoms, benzyl, cyclopropylmethyl group or a substituted or unsubstituted benzyloxy group. Galantamine mon-alkyl-carbamates are particularly useful.

11 Claims, 2 Drawing Sheets

(56) References Cited

OTHER PUBLICATIONS

Kintwell, Lars, et al. Sensory Abnormalities in Autism: A Brief Report. Research in Developmental Disabilities 32 (2011) 795-800.
Foss-Feig, Jennifer H., et al. Tactile Responsiveness Patterns and Their Association with Core Features in Autism Spectrum Disorders. Res Autism Spectr Disord. 2012; 6(1); 337-334.
Tomchek, Scott D., et al. Sensory Processing in Children With and Without Autism: A Comparative Study Using the Short Sensory Profile. Am J Occupational Therapy, Mar./Apr. 2007, vol. 61, No. 2, 190-200.
Blakemore, Sarah-Jayne, et al. Tactile sensitivity in Asperger Syndrome. Brian and Cognition, 61 (2006) 5-13.
Rob Nicolson, et al., "A Prospective, Open-Label Trial of Galantamine in Autistic Disorder", Journal of Child and Adolescent Psychopharmacology, 2006, vol. 16, No. 5, p. 621-629.
S.Y. Han, et al., "Cehmeical and pharmacological characterization of galanthamine, an acetycholinesterase inhibitor, and its dervatives, A potential application in Alzheimer's disease", Eur J Med Chem, 1992, vol. 27, p. 673-687.
The Office Action dated Feb. 21, 2019 in corresponding Japanese Patent Application No. 2017-502768 and the English translation thereof.
Soumee Bhattacharya, et al., "Galantamine Slows Down Plaque Formation and Behavioral Decline in the 5XFAD Mouse Model of Alzheimer's Disease", PLOS One, vol. 9, No. 2, Feb. 21, 2014, p. e89454, XP555287894.
B. Winblad, et al., "Safety and efficacy of galantamine in subjects with mild cognitive impairment—The GAL-NT-11/18-Study Group*", Jan. 1, 2008, XP055528615, URL:http://n.neurology.org/content/neurology/70/22/2024.full.pdf [title, abstract].
Zarra et al., "Efficacy and Safety of Galantamine in Long-term Treatment for Mild Cognitive Impairment", Alzheimers's & Dementia: The Journal of the Alzheimer's Association, Jan. 1, 2012, pp. P586-P586, XP0555287716 [title, abstract, conclusion].
Search Report issued in corresponding European Patent Application No. EP16797237.

* cited by examiner

TREATMENT OF AUTISM

RELATED APPLICATION

This application is a national phase entry under 35 USC 371 of International Patent Application No.: PCT/US2015/022220 filed on 24 Mar. 2015, which claims priority from US 61/969,896 filed on 25 Mar. 2014, the disclosures of which are incorporated in their entirety by reference herein.

FIELD OF THE INVENTION

The present invention relates to a method of treating patients with autism.

BACKGROUND OF THE INVENTION

Autistic Spectrum Disorders (ASD) are a group of developmental disorders including autistic disorder, Asperger disorder and pervasive developmental disorder not otherwise specified, according to the Diagnostic and Statistical Manual of the American Psychiatric Association, Fourth Edition. The disorders have in common social disconnection and repetitive or stereotyped behaviors. In autistic disorder there is delayed or impaired language (http://www.cdc.gov/ncbddd/autism/hcp-dsm.html). There are many specific genetic and environmental factors associated with ASD which lead to a similar behavioral outcome. An intermediate phenotype appears to be a reduction in nicotinic cholinergic receptors in certain parts of the brain.

Perry et al (Am J Psychiatry 2001, 158:1058) compared autopsy brain tissue among 26 normal, autistic, Down's and other mental retardation patients, aged about 24-36 years. In the frontal and parietal cortices, $\alpha_4\beta_2$ nicotinic receptors, as assessed by epibatidine binding, were reduced by about ⅔ in the autistic and mental retardation patients as compared to normal. The same laboratory compared nicotinic receptors in the thalamus, in which they are concentrated, in 3 autistic and 3 normal autopsy brains from patients aged 19-37. In the paraventricular and reuniens nuclei, $\alpha_7$ and $\beta_2$ reactive neurons were decreased in the autistic patients' brains, although $a_4$ immunoreactive neurons were not. (Ray et al, Neurobiol Disease, 2005, 19, 366) Based on the lack of activation of the "fusiform face area" known to occur when ASD patients are presented with strangers' faces, and the known cholinergic regulation of this area, PET studies of acetylcholinesterase activity were conducted in 20 young adult normal and ASD subjects, matched for I.Q. (Suzuki et al, Arch Gen Psychiatry 2011, 68, 3, 306) The ASD subjects had lower [$^{11}$C]MP4A $k_3$ values than controls, and those $k_3$ values correlated inversely with their social disabilities as assessed by the Autism Diagnostic Observation Schedule as well as the Autism Diagnostic Interview-Revised. The authors conclude that the fusiform face area has deficient cholinergic innervation in ASD subjects and that this relates to their level of social functioning. Case reports, open-label and poorly documented studies of galantamine, a cholinesterase inhibitor and positive allosteric modulator of nicotinic receptors, in ASD have reported some beneficial results. (Niederhofer et al, BMJ 2002, 325, 1421; Hertzberg, Int J Psychiatry in Medicine 2003/2004, 33, 4, 395; Nicholson et al, J Child Adolesc Psychopharmacol 2006, 16, 5, 621) A review of cholinergic abnormalities in ASD suggests that nicotinic agonists and positive allosteric modulators might be helpful, and then summarizes studies of donepezil, rivastigmine and galantamine in ASD. (Deutsch et al, Clin Neuropharm 2010, 33, 114).

There is a genetic copy number variation which can impair the formation of $\alpha_7$ nicotinic receptors. This occurs in 15q113.3, and is associated with autism, mental retardation, schizophrenia and epilepsy. (Yasui et al, Hum Molec Genetics 2011, 20, 22) Within this segment of chromatin is a region whose deletion causes the Prader-Willi Syndrome. When the protein whose deletion causes Rett Syndrome, MeCP2, binds to this region, it overlaps the Prader-Willi region and these map to sites flanking CHRNA7, which encodes the nicotinic $\alpha_7$ receptor. This finding led to the analysis of frontal cortices from Rett and autism patients for CHRNA7 expression, and a decrease averaging 40%, most obvious at young ages, was found in comparison to controls. (FIG. 1) The finding of the 15q13.3 deletion syndrome in a patient with uncontrollable rage outbursts led to a trial of galantamine. (Cubells et al, Am J Med Genet Part A 2011, 155, 805) A striking decrease in episodes of rage was reported, although environmental changes could also have been responsible.

Mutations in the Mecp2 gene are found in the great majority of cases of Rett syndrome. However, reduced Mecp2 effects have been reported more broadly in autism spectrum disorders. In the valproic acid model of autism, Mecp2 expression is decreased in neural progenitor cells of both sexes and in the prefrontal cortex of males, who comprise most cases of autism. (Kim K C et al, Mol Neurobiol 2014, Nov. 18 (epub ahead of print)) In the cerebellum of autistic patients, decreased Mecp2 binding has been reported and hypothesized to be the cause of the failure of downregulation of the Engrailed-2 gene, which is overexpressed. (James S J, et al, Transl Psychiatry 2014, 4:e460, Doi: 10.1038/tp.2014.87)

In human postmortem cortical tissue, significantly reduced Mecp2 expression was found in 79% of cases of autism (11/14), 100% of Rett (9/9), 100% of Angelman, 75% of Prader Willi (3/4), 60% of Down's syndromes (3/5), and in both of 2 cases of attention deficit hyperactivity disorder, as compared to normal age-matched controls. (Nagarajan R P, et al, Epigenetics 2006, 1(4):e1-11).

Galantamine has the structure:

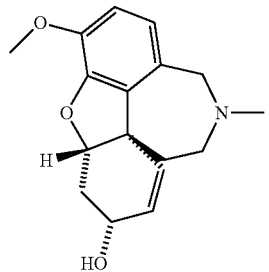

Galantamine is approved for the treatment of patients with mild to moderate Alzheimer's disease. It is not recommended for use in mild cognitive impairment due to increased mortality in that population.

U.S. Pat. No. 4,663,318, describes the use of galantamine, a known cholinesterase inhibitor, in the treatment of Alzheimer's disease. PCT publication WO 8808708, describes the use of analogs of galantamine and lycoramine for a similar purpose. U.S. Pat. No. 6,670,356, escribes the effects of analogs of galantamine and lycoramine in modulation of nicotinic receptors and in treating and retarding the progression of Alzheimer's and Parkinson's diseases, neuroprotection against neurodegenerative disorders. At the time of these patents, Alzheimer's disease understood to be a condition that manifested itself by dementia and its underlying causes were only beginning to be understood. The treatments described in these earlier patents addressed factors involved in such dementia, namely reducing the activity of acetylcholinesterase so as to limit the reduction in availability of the neurotransmitter acetylcholine that arises from the action of acetylcholinesterase thereon and indirect stimulation of nicotinic receptors by allosteric modulation thereof to improve their functioning.

The galantamine positive allosteric modulatory site is present on all nicotinic receptors which have been examined. (Samochocki et al, JPET 2003, 305, 1024) This mechanism may also be useful in the control of inflammation, pain, appetite, and depression.

SUMMARY OF THE PRESENT INVENTION

From a first aspect the present invention provides a method for treating patients with Autism Spectrum Disorders which comprises administering thereto a therapeutically acceptable dose of a compound of a galanthamine analog wherein the hydroxy group is replaced by a carbamate, carbonate or ester group and the methoxy group may be replaced by another alkoxy group of from two to six carbon atoms, a hydroxy group, hydrogen, an alkanoyloxy group or 2 to 10 carbon atoms, a benzoyloxy or substituted benzoyloxy group, a carbonate group of 1 to 10 carbon atoms or a carbamate group such as a mono alkyl or dialkyl or an aryl carbamate wherein the alkyl groups or aryl groups contain from 1 to 10 carbons; and the N-methyl group may be replaced by hydrogen, alkyl of 1 to 10 carbon atoms, benzyl, cyclopropylmethyl group or a substituted or unsubstituted benzoyloxy group.

Typically the group used to replace the hydroxyl group will be an alkanoyloxy group or 2 to 10 carbon atoms, a benzoyloxy or substituted benzoyloxy group, a carbonate group of 1 to 10 carbon atoms or a carbamate group such as a mono alkyl or dialkyl or an aryl carbamate wherein the alkyl groups or aryl groups contain from 1 to 10 carbons. Ester and carbamate groups are particularly useful. Commonly, the methoxy and methyl groups of galantamine will be left unchanged. Mono alkyl carbamates of 2 to 8 carbon atoms may be particularly useful.

In this first embodiment of the invention, a therapeutic dose of an active compound as described above is administered to patients having an autism spectrum disorder, as defined in DSM IV, in order to improve cognition or function or behavior. Improvements may be measured by the Aberrant Behavior Checklist, Autism Diagnostic Observation Schedule, Autism Diagnostic Interview Revised, Conner's Parent Rating Scale, Children's Psychiatric Rating Scale, Clinical Global Impression, or the like. The dose of a galantamine analog will be 0.2 to 100 mg, preferably 2-10 mg, or 1-50 mg, adjusted for the age and size of the person being treated.

DETAILED DESCRIPTION OF THE INVENTION

Figure 1:
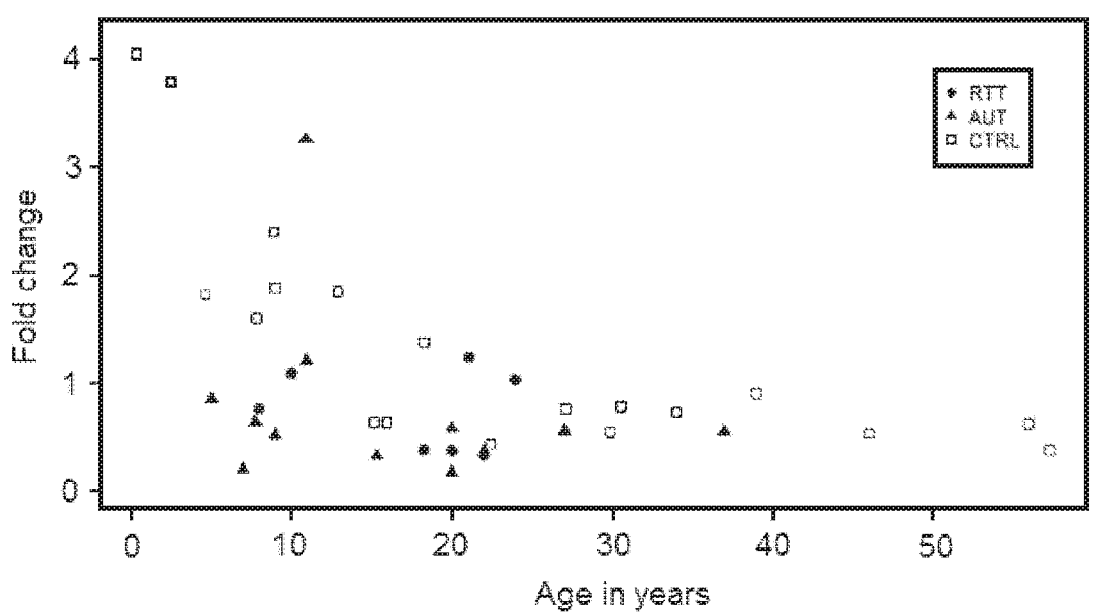
FIG. 1. CHRNA7 transcripts levels decline significantly with age in the human cortex. (Yasui et al, Hum Molec Genetics 2011, 20, 22, 4311).

One particularly useful compound is the n-butylcarbamate derivative of galantamine, having the structure:

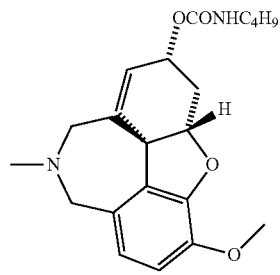

The $IC_{50}$ for galantamine n-butylcarbamate is $10.9 \times 10^{-7}M$ as compared to $3.97 \times 10^{-7}M$ for galantamine.

This compound was first described in Han et al as a cholinesterase inhibitor in Bioorg. & Medicinal Chemistry Letters 1, 11 579-580 (1991).

The pathways by which galantamine cleared Aβ, and protected neurons against Aβ, glutamate and SERCA inhibition toxicity, can be activated by analogs which preserve the nicotinic positive allosteric modulatory properties of the molecule, while markedly reducing cholinesterase inhibition. Galantamine butylcarbamate has about 36% of the enzymatic activity of galantamine.

Primary cultured rat neurons can be depolarized by the application of 1.5 mM choline. (Popa et al, J Mol Neurosci 2006, 30, 27). This is mediated by $\alpha_7$ nicotinic receptors, as it could be blocked by methyllyaconitine and α-bungarotoxin. Galantamine n-butylcarbamate, 1 μM, enhanced the depolarization caused by choline (15.9–2.1%). This was not significantly different from the effect of galantamine at the same concentration (20.6±4.2%). The enhancement produced by the n-butylcarbamate was blocked by the antibody to the galantamine recognition site on nicotinic receptors, FK-1, indicating that it was mediated by the galantamine positive allosteric modulatory site. Galantamine n-butylcarbamate is thus a positive allosteric modulator at the galantamine site, with an effect similar to that of galantamine.

The butylcarbamate differed from galantamine in adverse effects. (Han et al Eur J Med Chem 1992, 27, 673) Decreased motility which appeared at 5 mg/kg in galantamine-treated animals was not observed up to30 mg/kg of the analog. At doses of 50-100 mg/kg of the n-butylcarbamate, mice were wobbly and off-balance with rapid heart rate still present at 4 hours, but were recovered at 24 hours. There was no lethality up to 100 mg/kg. The LD50 of galantamine is 10 mg/kg. Mice injected IP with 10, 15 and 20 mg/kg galantamine develop seizures at an average of 8, 6 and 4 minutes respectively (Fonek et al, Neurosci 2003, 23, 7, 2582).

Galantamine n-butylcarbarmate is predicted to have 80% oral bioavailability, based on in vitro permeability of a layer of CaCo-2 cells, derived from a human colorectal carcinoma as shown below.

| Client ID | test conc (µM) | Assay duration (hr) | mean A -> B $P_{app}^a$ ($10^{-6}$ cm s$^{-1}$) | comment |
|---|---|---|---|---|
| Ranitidine | 50 | 2 | 1.1 | low permeability control |
| Warfarin | 50 | 2 | 34.7 | high permeability control |
| Galanthamine Carbamate | 50 | 2 | 20.8 | |

$^a$Apparent permeability

In an in-vitro preparation of liver microsomes, the half-life of galantamine n-butylcarbamate was greater than 60 minutes.

As shown below, this suggests that the compound is not metabolized to a substantial degree in the liver.

| Client ID | test conc (µM) | test species | NADPH-dependent $CL_{int}^a$ (µl min$^{-1}$ mg$^{-1}$) | NADPH-dependent $T_{1/2}^b$ (min) | NADPH-free $CL_{int}^a$ (µl min$^{-1}$ mg$^{-1}$) | NADPH-free $T_{1/2}^b$ (min) | comment |
|---|---|---|---|---|---|---|---|
| Verapamil | 5.0 | Mouse | 99.8 | 2.32 | 1.8 | >60 | metabolized control |
| Warfarin | 5.0 | Mouse | >1000 | >60 | 0.0 | >60 | non-metabolized control |
| Galanthamine HBr | 5.0 | Mouse | 0.0 | >60 | 0.0 | >60 | |
| Galanthamine Carbamate | 5.0 | Mouse | 23.5 | 98.2 | 0.0 | >60 | |

$^a$Microsomal Intrinsic Clearance
$^b$Half-life

Galantamine n-butylcarbamate is stable for greater than two hours in mouse plasma. Concentrations at two hours are slightly lower than those of galantamine, which has a plasma half-life of about 7 hours in human patients.

Mice with lesions of the nucleus basalis magnocellularis (nBrn) have poor memory for the fact that if they cross from a lighted compartment into a dark one, which they prefer, they will receive a shock through the floor grid. When given galantamine butylcarbamate during training, mice will remain in the lighted compartment about 100 seconds longer than when given saline. (Han et al, 1992, op cit) As shown in FIG. 3, the best dose for this memory enhancement is 0.5 mg/kg.

Figure 2:
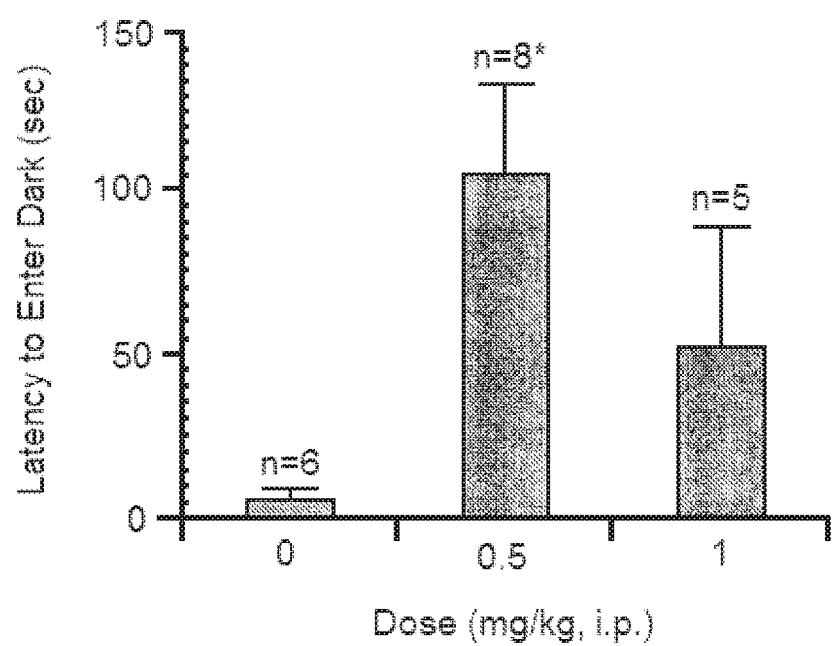
FIG. 2. is a bar graph showing that galantamine n-butyl-carbamate enhances passive avoidance learning. Galatamine n-butyl carbamate injected 3.5 hours before acquisition improves the 24 hour retention of B-F lesioned miceon a passive avoidance test. The bar graph shows mean scores (±SEM) and the number of subjects per dose. The latencies varied significantly with drug dose F=3.82, P=0.041*) and the 0.5 mg/kg dose was significantly better than other dose (Scheffe's F-test=3.88, P<0.05) (Han et al, Eur J Med Chem 1992, 27, 673).

A similar effect is seen with galantamine. However, optimal performance is an increase of about 125 seconds, and the best dose is 3 mg/kg, 6× that of the n-butylcarbamate. (FIG. 2) In summary, galantamine n-butylcarbamate, based on animal and in-vitro studies, appears to be well tolerated, safe, orally bioavailable, stable in plasma, and effective in enhancing learning at lower doses than galantamine. It enhances neuronal electrophysiological activity via the galantamine positive allosteric modulatory site on nicotinic receptors.

Compositions suitable for use in treatments according to the invention are typically suitable for oral administration such as tablets, capsules, or lozenges containing from 0.1 to 40 mg. of the active compound depending upon the activity and half-life of the compound. Compositions using the butylcarbamate will typically contain, for example in the range 1 to 10 mg, or 2 to 25 mg, or 5 to 40 mg per dose.

Oral dosage forms may be sustained dosage formulations in which the particles of the active compound are coated so as to delay release into the blood stream for example by coating with a pharmaceutically acceptable polymer that is dissolved in gastric juices such as polyvinyl pyrrolidone and then sizing the particles and incorporating specific ratios of particles of particular sizes into a tablet, capsule or lozenge so that particles having different degrees of thickness of coating are released at different times. In the present case, the coating technique will desirably result in most of the active compound being released within elve hours of administration. Alternative means of application may include for example transdermal patches in which case the objective is to provide administration of a dosage at a rate of . . . to 0.01 to 10 mg per hour.

Other dosage forms may be used if desired. For example nasal or parenteral including dosage formulations to assist passage of the blood-brain barrier.

For the purpose of nasal or parenteral therapeutic administration, the active compounds of the invention may be incorporated into a solution or suspension. These preparations typically contain at least 0.1% of active compound, for example between 0.5 and about 30% of the weight thereof. Preferred compositions and preparations according to the present inventions are prepared so that a nasal or parenteral dosage unit contains between 0.1 to 10 milligrams of active compound.

The solutions or suspensions may also include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants such as ascorbic acid or sodium bisulfate; chelating agents such as ethylene-diamine tetraacetic acid; buffers such as acetates; citrates or phosphates and agents for the adjustment of tonicity such as sodium chloride or dextrose. Parenteral multiple dose vials may be of glass or plastic.

Typical dosage rates in administration of the active ingredients depend on the nature of the compound that is used and in intravenous administration are in the range of 0.01 to 2.0 mg per day and per kilogram of body weight based on the physical condition and other medications of the patient.

Liquid formulations for nasal or intra-cerebroventricular administration at a concentration of 0.1 to 5 mg of active ingredient/ml. The compounds according to the invention can also be administered by a transdermal system, in which 0.1 to 10 mg/day is released. A transdermal dosage system may consist of a storage layer that contains 0.1 to 30 mg of the active substance as a free base of salt, in case together with a penetration accelerator, e.g., dimenyl sulfoxide, or a carboxylic acid, e.g., octanoic acid, and a realistic-looking polyacrylate, e.g., hexylacrylate/vinyl acetate/acrylic acid copolymer including softeners, e.g., isopropylmyristate. As a covering, an active ingredient-impermeable outside layer, e.g., a metal-coated, siliconized polyethylene patch with a thickness of, for example, 0.35 mm, can be used. To produce an adhesive layer, e.g., a dimethylamino-methacrylate/methacrylate copolymer in an organic solvent can be used.

The determination of a particular dose for any given patient will be a matter for the judgment of the physician treating the patient. However, suitable dosages may be determined by starting with a low dose and increasing if there is insufficient response. As noted above, these dosages may be considerably lower than the typical 0.2 to 100 mg, such as 0.2 to 10 mg, or 1 to 50 mg.

A good animal model is the Mecp2$^{1/ox}$ (now Mecp2 J) or Mecp2 R168x mouse. Males in particular have abnormal development, motor activity, anxiety, rotorod performance, fear conditioning and object recognition which can be assessed during treatment. (Stearns et al, Neuroscience 2007, 146, 907; Katz and Berger-Sweeney, Dis Model Mech 2012, 5, 6, 733). Other Mecp2 transgenic mice may be useful as well (Robinson et al, Brain 2012, 135, 9, 2699).

EXAMPLES

As noted in the Background section of this application, reduced Mecp2 effects have been reported more broadly in autism spectrum disorders. Therefore, animals with mutations in the Mecp2 gene were chosen to model the deficits which are present in the broader autism spectrum population.

Galantamine n-butylcarbamate affects cardiac and motor functions at very high doses (50 and 100 mg/kg). These negative side effects could be especially detrimental in autistic patients who have other disabilities and who may respond best to treatment administered very early in development. Because the cholinergic system (which is Modulated by galantamine n-butylcarbamate) affects both motor and respiratory functions, we monitored locomotor and respiratory functions in response to the drug treatment. In order to assess cognitive function in response to the drug treatment, we used a novel object recognition task because this task is one of the most consistent tasks in Which female Mecp2 mice show significant deficits (Stearns et al. 2007 Neuroscience 146: 907-921 PMID 17383101; Katz, Berger-Sweeney et al., 2012 Disease Model Mech 5: 733-45. PMID 23115203).

Locomotor activity was monitored using methods described previously (Shaevitz et al. 2013 Genes Brain Behav, 12(7): 732-40. doi: 10.1111/gbb.12070). Mecp2 mutant males (between 1 and 3 months old) and females (between 3 and 6 months old) and age-matched controls were monitored for one-hour prior to and 12 hours after drug (or vehicle: 20% DMSO in saline) administration (one set of mice received IP injections and one set of mice received oral gavage) in doses that ranged from 0.1-20 mg/kg). Activity was measured across the 12-h dark cycle using a photobeam activity system (San Diego instruments, San Diego, Calif., USA). Mice were placed individually into a cage (47×25×21 cm) inside a rectangular arena equipped with a 3×8 array of photobeams. The average number of ambulatory (two adjacent) and fine (repeated single) beam breaks per hour over the 12 h was compared. [N=2 mice/group at each dose and each administration route; for the vehicle controls, N=6 WT/group; N=6 Mecp2/group]. Data were analyzed using repeated measures analysis of variance.

Respiratory function was monitored in a plethysmograph (EMKA Technologies) for 30 minutes prior to and 1 hour after drug administration (one set of mice received IP injections and one set of mice received oral gavage). [N=2 mice/group at each dose and each administration route; for the vehicle controls, N=6 WT/group; N=6 Mecp2/group]. Data were analyzed using repeated measures analysis of variance.

Doses of the drug that did not impair motor or respiratory functions were then considered to be safe and well tolerated.

Cognitive function was assessed using the novel object recognition (NOR) task using methods previously described (Schaevitz et al. 2013). Female mice were tested because best practice suggests that pre-clinical trials of drugs should emphasize results in female models given that RTF is most prevalent in girls (Katz, Berger-Sweeney et al., 2012 Disease Model Mech 5:733-45. PMID: 23115203). Novel object memory was assessed during three sessions. This task relies on the innate tendency of a mouse to explore unfamiliar objects vs. familiar objects. Testing was performed in an open-field arena. Twenty-four hours prior to training, mice were habituated to the arena for 10 min. Ninety minutes before training, the mice were administered drug or vehicle (0.1, 0.5, 1.0, 2.5 and 5.0 mg/kg IP). During training, mice were given 10 min to explore two identical Lego objects (A+A). Short- and long-term object memory were assessed in two subsequent sessions (24 h after the completion of training) during which mice were given 10 min to explore the familiar (A) or a novel (B or C) object. The duration of exploration (defined as the mouse's snout or forelimbs physically touching or approaching within 1 cm of an object) of familiar and novel objects was measured. The amount of time spent exploring the novel object over the total time exploring both novel and familiar objects in each session was used to measure object memory. [N=6/dose of 0.1, 0.5 and 1.0; N=1/dose of 2.5 and 5.0 mg/kg; for vehicle N=6 WT and N=6 Mecp2 mice.] Given the small number of mice tested at each dose, we combined mice into groups of Mecp2 or controls, and vehicle or drug-treated Mecp2 mice and analyzed data the using Chi-squared analyses to determine whether there were differences amongst group of those that learned the NOR task and those that did not.

Results

Ambulatory and fine motor movements were not significant altered at any of the doses of the drug tested. We have shown previously (Schaevitz et al. 2013) that ambulatory movements in Mecp2 males is significantly lower than in wildtype mice; in Mecp2 females were also significantly lower than wildtype, but the impairment was milder. Doses of the drug (administered either IP or by gavage between 0.1 and 20 mg/kg) did not impair locomotor activity in the Mecp2 mice of either sex. Also, the same doses and administration routes of the drug did not affect respiratory activity. Therefore, the drug was safe and well tolerated at doses between 0.1 and 20 mg/kg in Mecp2 mice of both sexes, as well as controls.

For the novel objection recognition task data, we created a matrix of all wildtype and Mecp2 females who were administered the vehicle and a second matrix comparing Mecp2 females with and without the drug (all doses combined). Mice were divided into two categories: those who learned the novel object task (had object recognition scores above chance level>0.5) and those that did not learn the novel object task (had object recognition scores at or below chance levels≤0.5). We asked two questions:

1) Do the Mecp2 females (administered vehicle) perform significantly worse than WT controls on the task?

|  | NOR scores = or below 0.5 | NOR scores above 0.5 |
| --- | --- | --- |
| Mecp2 | 83% | 17% |
| WT | 33% | 67% |

The wildtype mice learned the NOR task but the Mecp2 mice did not learn the task [Chi square, (df=1, N=12)=6.75, p=0.0094].

2) Does galantamine n-butylcarbamate improve performance in the Mecp2 mice on the task?

|  | NOR scores = or below 0.5 | NOR scores above 0.5 |
| --- | --- | --- |
| Mecp2 (Vehicle) | 83% | 17% |
| Mecp2 (drug) | 65% | 35% |

The Mecp2 mice treated with galantamine n-butylcarbamate learned the NOR task significantly better than vehicle-injected Mecp2 mice [Chi square, (df=1, N=12)=4.592, p=0.0321].

Therefore, our data show that galantamine n-butylcarbamate improves memory for a novel object and cognitive performance in a female mouse model of RTT syndrome at doses that do not impair locomotor activity or respiratory functions.

The invention claimed is:

1. A method for treating Autism Spectrum Disorders in patients suffering therefrom which comprises administering to a patient in need thereof a therapeutically effective dose of a galantamine analog wherein
   the hydroxy group is replaced by a carbamate or carbonate group;
   the methoxy group is optionally replaced by another alkoxy group of from two to six carbon atoms, a hydroxy group, hydrogen, an alkanoyloxy group of 2 to 10 carbon atoms, a benzoyloxy or substituted benzoyloxy group, a carbonate group of 1 to 10 carbon atoms or a carbamate group such as a mono alkyl or dialkyl or an aryl carbamate wherein the alkyl groups or aryl groups have from 1 to 10 carbons; and the N-methyl group is optionally replaced by hydrogen, alkyl of 1 to 10 carbon atoms, benzyl, cyclopropylmethyl group or a substituted or unsubstituted benzoyloxy group.

2. A method as claimed in claim 1, wherein the hydroxyl group of galantamine is replaced by a carbonate group of 1 to 10 carbon atoms or a carbamate group such as a mono alkyl or dialkyl or an aryl carbamate wherein the alkyl groups or aryl groups have from 1 to 10 carbons.

3. A method as claimed in claim 1, wherein the hydroxy group of galantamine is replaced by a mono alkyl carbamate group of 2 to 8 carbon atoms.

4. A method as claimed in claim 3, wherein the hydroxy group of galantamine is replaced by an n-butyl carbamate group.

5. A method as claimed in claim 1, wherein the methoxy and methyl groups of galantamine are unchanged.

6. A method as claimed in claim 4, wherein the methoxy and methyl groups of galantamine are unchanged.

7. A method as claimed in claim 1, wherein the dose of a galantamine analog is from 0.2 to 100 mg.

8. A method as claimed in claim 4, wherein galantamine n-butyl carbamate is administered in dosages of 1 to 10 mg-per dose.

9. A method as claimed in claim 1, wherein the galantamine analog is administered as an oral dosage form in which the particles of the galantamine analog are coated so as to delay release into the blood stream by coating with a pharmaceutically acceptable polymer that is dissolved in gastric juices.

10. A method as claimed in claim 4, wherein galantamine n-butyl carbamate is administered in dosages of 2 to 25 mg per dose.

11. A method as claimed in claim 4, wherein galantamine n-butyl carbamate is administered in dosages of 5 to 40 mg per dose.

* * * * *